United States Patent
Strerath et al.

(10) Patent No.: US 12,362,042 B2
(45) Date of Patent: Jul. 15, 2025

(54) IDENTIFYING THE PAIRING OF VARIABLE DOMAINS OF LIGHT AND HEAVY CHAINS OF ANTIBODIES

(71) Applicant: BAYER AKTIENGESELLSCHAFT, Leverkusen (DE)

(72) Inventors: Michael Strerath, Düsseldorf (DE); Christian Bender, Bergisch-Gladbach (DE); Johanna Völker, Berlin (DE); Julio Cesar Bolivar Lopez, Düsseldorf (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 1308 days.

(21) Appl. No.: 17/048,533

(22) PCT Filed: Apr. 16, 2019

(86) PCT No.: PCT/EP2019/059728
§ 371 (c)(1),
(2) Date: Oct. 16, 2020

(87) PCT Pub. No.: WO2019/206729
PCT Pub. Date: Oct. 31, 2019

(65) Prior Publication Data
US 2021/0166787 A1    Jun. 3, 2021

(30) Foreign Application Priority Data

Apr. 25, 2018 (EP) .................................. 18169334

(51) Int. Cl.
| | |
|---|---|
| G16B 40/20 | (2019.01) |
| C07K 16/00 | (2006.01) |
| C12N 15/10 | (2006.01) |
| G16B 5/00 | (2019.01) |
| G16B 20/00 | (2019.01) |

(52) U.S. Cl.
CPC ............ *G16B 40/20* (2019.02); *C07K 16/005* (2013.01); *C12N 15/1037* (2013.01); *G16B 5/00* (2019.02); *G16B 20/00* (2019.02)

(58) Field of Classification Search
None
See application file for complete search history.

(56) References Cited

U.S. PATENT DOCUMENTS

2013/0178370 A1    7/2013    Lavinder et al.

OTHER PUBLICATIONS

Greiff et al. "Learning the High-Dimensional Immunogenomic Features That Predict Public and Private Antibody Repertoires", J Immunol 199 (8) pp. 2985-2997, published Oct. 15, 2017 (Year: 2017).*

Linling He et al., Hidden Lineage Complexity of Glycan-Dependent HIV-1 Broadly Neutralizing Antibodies Uncovered by Digital Panning and Native-Like gp140 Trimer, *Frontiers In Immunology*, vol. 8, Aug. 24, 2017 (Aug. 24, 2017), DOI: 10.3389/fimmu.2017. 01025, XP055516159.

Reddy Sai T et al., Monoclonal antibodies isolated without screening by analyzing the variable-gene repertoire of plasma cells, *Nature Biotechnology*, Gale Group Inc., New York, vol. 28, No. 9, Sep. 1, 2010 (Sep. 1, 2010), pp. 965-969, 1 DOI: 10.1038/NBT.1673, ISSN: 108709156, XP002693037.

* cited by examiner

*Primary Examiner* — Nancy J Leith
*Assistant Examiner* — Jessica D Parisi
(74) *Attorney, Agent, or Firm* — Harness, Dickey & Pierce, P.L.C.

(57) ABSTRACT

The present invention relates to the identification of antibodies and/or antibody fragments in a selection process. The present invention relates to a method, a system and a computer program product for identifying pairs of genes which encode the variable domains of light and heavy chains of selected antibodies and/or antibody fragments.

18 Claims, 7 Drawing Sheets

(1)   $(A(V_H^y) <= 9)$ and $(A(V_L^x) <= 1) \rightarrow$ CLASS=neg (2)   $(A(V_L^x) <= 36)$ and $(relV_L^x <= 0.000019)$ and $(A(V_H^y) <= 559) \rightarrow$ CLASS=neg (3)   $(A(V_L^x) <= 37)$ and $(relV_L^x <= 0.000014) \rightarrow$ CLASS=neg (4)   $(A(V_H^y) <= 3)$ and $(prevA(V_L^x) <= 113) \rightarrow$ CLASS=neg (5)   $(A(V_H^y) <= 19)$ and $(relV_H^y <= 0.000098)$ and $(prevA(V_L^x) <= 347)$ and $(numV_L >= 260490) \rightarrow$ CLASS=neg (6)   $(A(V_H^y) <= 5)$ and $(relV_L^x <= 0.00022) \rightarrow$ CLASS=neg (7)   $(relV_L^x <= 0.00023)$ and $(V_L^x <= 11) \rightarrow$ CLASS=neg (8)   $(A(V_H^y) <= 5)$ and $(prevA(V_H^y) <= 4) \rightarrow$ CLASS=neg (9)   $(A(V_H^y) <= 4)$ and $(numV_H >= 316361) \rightarrow$ CLASS=neg

(10)  $(A(V_L^x) <= 160)$ and $(relV_L^x <= 0.000101)$ and $(prevA(V_L^x) <= 61)$ and $(maxV_L <= 734492) \rightarrow$ CLASS=neg

(11)  $(A(V_H^y) <= 39)$ and $(prevA(V_L^x) <= 9)$ and $(prevA(V_H^y) <= 170) \rightarrow$ CLASS=neg

(12)  $(A(V_L^x) <= 113)$ and $(relV_L^x <= 0.000228)$ and $(prevnum <= 1) \rightarrow$ CLASS=neg

(13)  $(relV_H^y <= 0.000467)$ and $(A(V_H^y) <= 6)$ and $(relV_L^x <= 0.001555) \rightarrow$ CLASS=neg

(14)  $(A(V_L^x) <= 242)$ and $(prevA(V_H^y) <= 3)$ and $(relV_L^x <= 0.001307) \rightarrow$ CLASS=neg $\rightarrow$ CLASS=pos

Fig. 7

IDENTIFYING THE PAIRING OF VARIABLE DOMAINS OF LIGHT AND HEAVY CHAINS OF ANTIBODIES

CROSS-REFERENCE TO RELATED APPLICATIONS

This application is a U.S. national stage filing under 35 U.S.C. § 371 of International Application No. PCT/EP2019/059728 filed on Apr. 16, 2019, which claims the benefit of and priority to European Application No. 18169334.2 filed on Apr. 25, 2018. The entire disclosure of each of the above applications is incorporated herein by reference.

The present invention deals with the identification of antibodies and/or antibody fragments in a selection method. Subjects of the present invention are a method, a system and a computer program product for identifying pairs of genes which encode the variable domains of light and heavy chains of selected antibodies and/or antibody fragments.

The human immune system forms a complex network of various organs, cell types and molecules as a defence system against exogenous invaders.

Antibodies, also called immunoglobulins, are proteins from the class of the globulins that are formed in vertebrates as a response to certain substances, what are known as antigens. Antibodies serve the immune system; they are produced by a class of white blood cells, the B lymphocytes.

What act as antigens are almost exclusively macromolecules or particle-bound molecules, for example lipopolysaccharides on the surface of bacteria. A particular antigen generally induces the formation of only a few particular antibodies, which in most cases only recognize, via specific, non-covalent bonds, this foreign substance.

The specific binding of antibodies to antigens forms a major part of the defence against foreign substances which have invaded.

Every antibody consists of two identical heavy chains (H) and two identical light chains (L), which are linked to one another by covalent disulfide bonds to form a Y-shaped structure. The light chains each consist of one variable domain and one constant domain. They are referred to as $V_L$ and $C_L$. The heavy chains by contrast each have one variable domain and three (IgG, IgA) or four (IgM, IgE) constant domains. By analogy, they are referred to as $V_H$ and $C_H1$, $C_H2$, $C_H3$.

The variable domains of one light chain and one heavy chain form the antibody binding site; they are therefore of particular interest for therapeutic, immunological and/or diagnostic purposes. Large libraries of antibodies and/or antibody fragments are created and evaluated for the use thereof in medicine.

A widespread technique for generating and characterizing antibody libraries is the "phage display" method, in which the particular protein of interest can be expressed as a fusion polypeptide on a bacteriophage coat protein and selected by binding to immobilized or soluble biotinylated ligands (antigens). A phage constructed in this manner can be regarded as a compact genetic unit which combines both the phenotypic properties and the genotypic properties. "Phage display" technology has been successfully applied to antibodies, antibody fragments, enzymes, DNA-binding proteins, etc.

To use, for example, a phage display of antibody libraries, the relevant cells are first isolated from the organism. These concern plasma cells, which are to be found especially in blood, bone marrow and lymph nodes. From these cells, mRNA is isolated, which is then transcribed into cDNA.

With the aid of the polymerase chain reaction (PCR), the genes of the variable domains of the light chain ($V_L$) and heavy chain ($V_H$) of the antibodies are replicated from the cDNA.

Each set of genes is ligated with the truncated gene of the coat protein pIII (minor coat protein) of the M13 phage in a specific phagemid vector and *Escherichia coli* is transformed therewith.

As a result, the *E. coli* bacteria express pIII fusion proteins containing scFv fragments or Fab antibody fragments. By means of a signal peptide, the fusion proteins are transported into periplasm, where they fold to form a functional scFv or disulfide bond-linked Fab fragment. The Fv or Fab portions initially remain anchored in the inner *E. coli* membrane via the pIII fragment and bind to the capsid when phage assembly is completed.

Via the coat protein pIII, which is normally responsible for bacteria infection, the functional antibody fragment is, after coinfection with an M13 helper phage, incorporated in the outer coat of newly formed phages during the maturation process thereof. At the same time, the phagemid containing the associated genetic information for the corresponding antibody fragment is incorporated in the interior of the newly formed phages. Thus, each of these recombinant phages has theoretically a different antibody fragment on its surface and, at the same time, the associated genes ($V_L$ and $V_H$) in its interior, comparable with the billions of B cells in the (human) body.

In a so-called biopanning procedure, the "binding" phages can be selected from the billion-fold background of irrelevant phages by interaction with fixed ligands (antigens) via the antibody fragments exposed on the surface.

Usually, biopanning involves passing through multiple selection cycles (panning rounds). Usually, this involves exposing a phage display library to a substrate so that the binding of some phages can take place. Non-specifically binding and weakly binding phages are washed off. Phages which are still binding after washing and are hence specific are subsequently detached (eluted). The eluted phages are multiplied and exposed to the substrate again in further panning rounds until there is an enriched population of efficiently binding phages.

At the end of the selection process, the associated antibody genes can be easily isolated and sequenced from the isolated phages. Sequencing then yields information about the blueprints of the antibody (fragments). Further methods for selecting antibodies and/or antibody fragments are described in the literature (see, for example, Sai T. Reddy et al.: *Monoclonal antibodies isolated without screening by analyzing the variable-gene repertoire of plasma cells*, Nature Biotechnology Vol. 28 No. 9, September 2010, 965-971).

A standard method for sequence determination is the Sanger dideoxy method (chain-termination synthesis). The length of the DNA segments sequenced in this way (reads) can reach more than 1000 base pairs, but this is associated with high costs and expenditure of time.

The diversity of phage display libraries is usually between $10^7$ and $10^{11}$. However, only a few hundred antibody genes are sequenced today using the Sanger sequencing method, i.e. it is only of a fraction of the $10^7$ to $10^{11}$ clones of a phage display library that the identity is determined.

An alternative is next-generation sequencing (NGS). Owing to the detection of many parallelly running and spatially separated sequencing reactions on a very small area, a distinctly higher throughput with shorter read lengths is rapidly achieved in comparison with the standard. NGS achieves a magnitude of $10^6$ sequencing reactions. This means that it is possible to determine the diversity and quality of an entire library.

Even for the selection process involving passage through multiple biopanning cycles, NGS technology offers a huge advantage over standard Sanger technology. Sanger sequencing only allows the determination of a few antibody genes, on the basis of which usually only the selection round used for a subsequent screening is identified. The possibility of NGS technology of being able to obtain sequence information of a multiplicity of clones, if not even all clones, would give a deep insight into the selection process and could even spare a subsequent screening step.

The challenge for next-generation sequencing systems is that of coping with the quantities of data that must be evaluated (bio)informatically. The multiplicity of sequenced gene segments must be correctly put together in order to be able to unambiguously determine the genes encoding the sought antibody.

One problem—precisely in the case of a large number of ascertained gene sequences—is identifying the correct $V_L$-$V_H$ pair. The variable domains of the light chain ($V_L$) and the heavy chain ($V_H$) of an antibody are encoded by different genes. If many gene segments are sequenced in the case of a selection method such as, for example, biopanning, what arises is a multiplicity of genes encoding the variable domains of the light and heavy chains. However, it is unclear which genes for light chains are to be combined with which genes for heavy chains in pairs in order to determine the correct $V_L$-$V_H$ pairs and hence the sought antibody.

US 2013/178370 A1 describes the identification of antibody fragments via phage display methods. This involves using next-generation sequencing to determine the genes. Pairings of $V_L$ and $V_H$ genes correlate with the order of the count of the associated proteins in a sample.

Linling et al. disclose a phage display method for identifying scFv antibody fragments which bind to HIV-1 antigens. Four selection cycles are carried out and, after each cycle, the plasmids are extracted from the bacteria and sequenced by means of NGS. The bioinformatics analysis includes the provision of HC and LC data sets. Nonredundant scFv clones are identified by putting together characteristic, unique HCDR3-LCDR3 pairs (*Hidden Lineage Complexity of Glycan-Dependent HIV-1 Broadly Neutralizing Antibodies Uncovered by Digital Panning and Native-Like gp140 Trimer*, Frontiers in Immunology, Vol. 8, 24 Aug. 2017 (Aug. 24, 2017), XP55516159, DOI: 10.3389/fimmu.2017.01025).

Sai T. Reddy et al. report that $V_L$-$V_H$ pairs can be found on the basis of the counts of the corresponding genes (*Monoclonal antibodies isolated without screening by anaylzing the variable-gene repertoire of plasma cells*, Nature Biotechnology Vol. 28 No. 9, September 2010, 965-971).

However, in practice, it has become apparent that identification of $V_L$-$V_H$ pairs solely by assignment of genes to one another on the basis of the counts with which they occur does not lead to a satisfactory result.

Proceeding from the described prior art, it is therefore an object to identify, from a multiplicity of genes for the variable domains of light and heavy chains, pairs of genes which encode $V_L$-$V_H$ pairs of antibodies.

According to the invention, this object is achieved by the subjects of the independent claims. Preferred embodiments can be found in the dependent claims and in the present description.

The present invention therefore provides, in a first aspect, a method comprising the steps of:

providing a library of antibodies and/or antibody fragments, introducing the antibodies and/or antibody fragments to a selection method, the selection method comprising at least two selection cycles, a first selection cycle and a second selection cycle, sequencing the genes of the antibodies and/or antibody fragments after the first selection cycle and after the second selection cycle and ascertaining $V_L$ genes encoding the variable domains of light chains of the antibodies and/or antibody fragments and $V_H$ genes encoding the variable domains of the heavy chains of the antibodies and/or antibody fragments, ascertaining features relating to the $V_L$ genes and $V_H$ genes from the first selection method and from the second selection method, the features relating to the $V_L$ genes and $V_H$ genes comprising the following features:

counts of the $V_H$ genes in the pool from the second selection cycle, counts of the $V_L$ genes in the pool from the second selection cycle, counts of the $V_H$ genes in the pool from the first selection cycle, and counts of the $V_L$ genes in the pool from the first selection cycle forming feature vectors for pairs of $V_L$ genes and $V_H$ genes from the second selection cycle on the basis of the ascertained features from the first selection cycle and the second selection cycle, introducing the feature vectors to a model, the model calculating a result for each pair of a $V_L$ gene and a $V_H$ gene on the basis of its feature vector, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment, outputting the result.

The present invention further provides a system comprising:

an input unit,
a control unit,
a feature vector generation unit,
a calculation unit and
an output unit, the control unit being configured to acquire features relating to $V_L$ genes and $V_H$ genes encoding variable domains of light and heavy chains of antibodies and/or antibody fragments via the input unit, the antibodies and/or antibody fragments originating from a selection method comprising at least two selection cycles, a first selection cycle and a second selection cycle, the features relating to the $V_L$ genes and $V_H$ genes comprising the following features:

counts of the $V_H$ genes in the pool from the second selection cycle, counts of the $V_L$ genes in the pool from the second selection cycle, counts of the $V_H$ genes in the pool from the first selection cycle, and counts of the $V_L$ genes in the pool from the first selection cycle, the control unit being configured to prompt the feature vector generation unit to form feature vectors for pairs of $V_L$ and $V_H$ genes from the second selection cycle on the basis of the acquired features, the control unit being configured to prompt the calculation unit to calculate a result for each pair of a $V_L$ gene and a $V_H$ gene on the basis of its feature vector with the aid of a model, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment, the control unit being configured to prompt the output unit to output the result.

The present invention further provides a computer program product comprising a data carrier, and program code which is stored on the data carrier and which prompts a computer, in the memory of which the program code is loaded, to execute the following steps:

acquiring features relating to $V_L$ genes and $V_H$ genes encoding variable domains of light and heavy chains of antibodies and/or antibody fragments, the antibodies and/or antibody fragments originating from a selection method comprising at least two selection cycles, a first selection cycle and a second selection cycle, the features relating to the $V_L$ genes and $V_H$ genes comprising the following features:

counts of the $V_H$ genes in the pool from the second selection cycle, counts of the $V_L$ genes in the pool from the second selection cycle, counts of the $V_H$ genes in the pool from the first selection cycle, and counts of the $V_L$ genes in the pool from the first selection cycle, forming feature vectors for pairs of $V_L$ and $V_H$ genes from the second selection cycle on the basis of the acquired features, calculating a result for a pair of a $V_L$ gene and a $V_H$ gene on the basis of its feature vector with the aid of a model, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment, outputting the result.

The invention will be more particularly elucidated below without distinguishing between the subjects of the invention. On the contrary, the following elucidations are intended to apply analogously to all the subjects of the invention, irrespective of in which context they occur.

If steps are stated in an order in the present description or in the claims, this does not necessarily mean that the invention is restricted to the stated order. On the contrary, it is conceivable that the steps can also be executed in a different order or else in parallel to one another, unless one step builds upon another step, this absolutely requiring that the building step be executed subsequently (this being, however, clear in the individual case). The stated orders are thus preferred embodiments.

One starting point for the present invention is a library of antibodies and/or antibody fragments. Said antibodies and/or antibody fragments are introduced to a selection method in order to select antibodies and/or antibody fragments on the basis of their phenotypic properties. The selection method can, for example, be a biopanning method. It can also be an immunization method, as described in Nature Biotechnology Vol. 28 No. 9, September 2010, 965-971, for example. Further selection methods are conceivable.

A selection method in the context of the present invention comprises multiple selection cycles. There are at least two selection cycles, a first selection cycle and a second selection cycle. The selection cycles can be arranged side by side and/or one above the other in a selection hierarchy. FIG. 1 shows an example of a selection hierarchy having three levels (I, II, III). In the first level (I), a library of antibodies and/or antibody fragments is introduced to a first selection cycle. The result of the first selection cycle is a pool of selected antibodies and/or antibody fragments. In the second level (II), the selected antibodies and/or antibody fragments are introduced to two selection cycles (a and b). Generally, the selection cycles in the second level are different selection cycles. The results of the selections in the second level are, in turn, two pools of selected antibodies and/or antibody fragments. In the third level (III), the pool of antibodies and/or antibody fragments that results from the right branch (IIb) of the second level is again exposed to two selection cycles (a and b), which, in turn, result in two pools. Generally, the antibodies and/or antibody fragments are exposed to an increasing selection pressure when passing through a selection hierarchy from top to bottom (e.g. from the first level to the third level via the second level). When passing through a selection hierarchy from top to bottom (e.g. from the first level to the third level via the second level), the diversity of the antibodies and/or antibody fragments in the respective pools decreases.

In a preferred embodiment, the first selection cycle and the second selection cycle are arranged immediately one above the other in the selection hierarchy of the selection method. Preferably, the second selection cycle is arranged immediately after the first selection cycle, i.e. the (selected) antibodies and/or antibody fragments originating from the first selection cycle are introduced to the second selection cycle (optionally after a multiplication step and further customary steps in a sequencing method).

However, it is also conceivable that the first selection cycle and the second selection cycle are arranged side by side in the selection hierarchy of the selection method.

Following a selection cycle, genes of the selected antibodies and/or antibody fragments are usually sequenced.

The goal of sequencing is to ascertain $V_L$ genes encoding the variable domains of light chains of the antibodies and/or antibody fragments and $V_H$ genes encoding the variable domains of the heavy chains of the antibodies and/or antibody fragments.

It is conceivable that such a sequencing step is carried out after each selection cycle. It is also conceivable that such a sequencing step is only carried out after passing through a hierarchy of multiple cycles. It is conceivable that a certain enrichment of specifically binding antibodies and/or antibody fragments is to be achieved first before a characterization by sequencing takes place. However, according to the invention, at least genes of the antibodies and/or antibody fragments in the pool from a first selection cycle and in the pool from a second selection cycle are sequenced.

In a further step of the method according to the invention, features relating to the $V_L$ and $V_H$ genes are acquired/ascertained.

According to the invention, at least features relating to the $V_L$ and $V_H$ genes from the first selection cycle and from the second selection cycle are acquired, since said features are combined together when forming feature vectors to identify $V_L$-$V_H$ pairs. It is conceivable to acquire features relating to the $V_L$ and $V_H$ genes from further selection cycles.

Important features relating to $V_L$ and $V_H$ genes are the counts with which they occur. The counts are preferably acquired by next-generation sequencing methods, by assembling the fragmented genetic information of $V_H$ and $V_L$ sequences to form complete $V_H$ and $V_L$ chains (or parts thereof) with the aid of paired recognition sequences (primer pairs). The unambiguous sequences are then counted and outputted in the form of DNA counts.

According to the invention, features (preferably counts) are acquired from multiple selection cycles and used for ascertaining $V_L$-$V_H$ pairs, in contrast to the method described in the prior art.

Besides counts, it is possible to acquire further features relating to the $V_L$ and $V_H$ genes. For example, these include also items of information about the substrates used in the selection cycles, parameters relating to carrying out the sequencing cycles (concentrations, temperatures, media, and others), structure of the sequencing hierarchy (number of levels and/or branches), and others.

The acquired features (such as, for example, the counts of the $V_L$ and $V_H$ genes) go into the generation of feature vectors in a subsequent step. Generally, a feature vector combines the (preferably numerically) parameterizable properties (features) of an object in a vectorial manner. Various features characteristic of the object form the various dimensions of said vector. The entirety of possible feature vectors is called the feature space. Feature vectors facilitate, for example, an automatic classification, since they greatly reduce the properties to be classified.

In the present case, the object is a pair of $V_L$ genes and $V_H$ genes. A feature vector can be generated for each pair of $V_L$ genes and $V_H$ genes. The feature vector characterizes the particular pair.

The following features can be incorporated in the feature vector for a pair of $V_L$ genes and $V_H$ genes:
- information about the observed $V_H$ gene (e.g. an unambiguous identifier)
- information about the observed $V_L$ gene (e.g. an unambiguous identifier)
- the absolute number (count) of the $V_H$ gene in the pool from the second selection cycle: $A(V_H)$
- the absolute number (count) of the observed $V_L$ gene in the pool from the second selection cycle: $A(V_L)$
- the absolute number (count) of different $V_H$ genes in the pool from the second selection cycle: $numV_H$
- the absolute number (count) of different $V_L$ genes in the pool from the second selection cycle: $numV_L$
- the absolute number (count) of that $V_H$ gene which is present in the pool from the second selection cycle with the greatest count: $maxV_H$
- the absolute number (count) of that $V_L$ gene which is present in the pool from the second selection cycle with the greatest count: $maxV_L$
- the relative count of the $V_H$ gene in the pool from the second selection cycle (based on the number of the $V_H$ gene which occurs in the pool from the second selection cycle with the greatest count): $relV_H = A(V_H)/maxV_H$
- the relative count of the $V_L$ gene in the pool from the second selection cycle (based on the number of the $V_L$ gene which occurs in the pool from the second selection cycle with the greatest count): $relV_L = A(V_L)/maxV_L$
- the difference (distance) between the count of the observed $V_H$ gene in the pool from the second selection cycle and the count of the observed $V_L$ gene in the pool from the second selection cycle (as amount): $diff = |A(V_H) - A(V_L)|$
- the relative difference (relative distance) between the count of the $V_H$ gene in the pool from the second selection cycle and the count of the $V_L$ gene in the pool from the second selection cycle (in relation to the count of that gene in the pool from the second selection cycle that occurs with a greater count): $reldiff = |A(V_H) - A(V_L)|/Max(A(V_H), A(V_L))$, where $Max(A(V_H), A(V_L)) = A(V_H)$ for $A(V_H) > A(V_L)$ and $Max(A(V_H), A(V_L)) = A(V_L)$ for $A(V_L) \geq A(V_H)$
- the number of selection cycles (levels) which were passed through before the second selection cycle: $prevnum$
- the absolute number of the $V_H$ gene in the pool from the first selection cycle: $prevA(V_H)$
- the absolute number of the $V_L$ gene in the pool from the first selection cycle: $prevA(V_L)$
- the difference (distance) between the count of the $V_H$ gene from the pool of the first selection cycle and the count of the $V_L$ gene from the pool of the first selection cycle (as amount): $prevdiff = |PrevA(V_H) - prevA(V_L)|$
- the relative change in the number of the $V_H$ genes from the first selection cycle to the second selection cycle: $prevRelDiffV_H = (|A(V_H) - prevA(V_H)|)/Max(A(V_H), prevA(V_H))$, where $Max(A(V_H), prevA(V_H)) = A(V_H)$ for $A(V_H) > prevA(V_H)$ and $Max(A(V_H), prevA(V_H)) = prevA(V_H)$ for $prevA(V_H) \geq A(V_H)$
- the relative change in the number of the $V_L$ genes from the first selection cycle to the second selection cycle: $prevRelDiffV_L = (|A(V_L) - prevA(V_L)|)/Max(A(V_L), prevA(V_L))$, where $Max(A(V_L), prevA(V_L)) = A(V_L)$ for $A(V_L) > prevA(V_L)$ and $Max(A(V_L), prevA(V_L)) = prevA(V_L)$ for $prevA(V_L) \geq A(V_L)$ It is conceivable that further items of information besides the stated features go into the generation of feature vectors. For example, counts of $V_H$ genes and $V_L$ genes in pools from further selection cycles can be acquired as features and go into the generation of feature vectors. As described above, features relating to selection hierarchy and/or parameters of the individual selection cycles can also be acquired and go into the generation of feature vectors.

The information about the observed $V_H$ gene (e.g. an unambiguous identifier) and the information about the observed $V_L$ gene (e.g. an unambiguous identifier) serve to identify the observed $V_H$ gene and the observed $V_L$ gene. An unambiguous identifier can, for example, be a gene sequence, a name, a code number, an alphanumerical identification code or some other identifier, by means of which a $V_L$ gene or a $V_L$ gene is unambiguously designated and hence made identifiable. The unambiguous identifiers are therefore primarily used for processing the results and for assigning the results to the corresponding $V_H$ and $V_L$ genes.

The feature vectors are introduced to a model. The model calculates for each feature vector which is introduced thereto whether the pair of a $V_L$ gene and a $V_H$ gene to which the feature vector is assigned encode variable domains of the light and heavy chains that belong to the same antibody and/or antibody fragment or do not belong to the same antibody and/or antibody fragment.

The model can, for example, be a classification model. Such a classification model assigns each pair of $V_L$ and $V_H$ genes on the basis of the of its feature vector to one of at least two classes. A first class encompasses those pairs encoding variable domains of the light and heavy chains that belong to the same antibody and/or to the same antibody fragment. A second class encompasses those pairs encoding variable domains of the light and heavy chains that do not belong to the same antibody and/or do not belong to the same antibody fragment.

Expressed simply, the classification model provides information about whether a $V_L$ gene and a $V_H$ gene belong together or not. They belong together when the $V_L$ gene encodes the variable domain of a light chain of an antibody and/or antibody fragment and the $V_H$ gene encodes the variable domain of a heavy chain of the same antibody and/or the same antibody fragment. In such a case, the pair of $V_L$ and $V_H$ genes is also referred to as a (correct) $V_L$-$V_H$ pair. They do not belong together when the $V_L$ gene encodes the variable domain of a light chain of an antibody and/or antibody fragment and the $V_H$ gene encodes the variable domain of a heavy chain of a different antibody and/or a different antibody fragment.

It is conceivable that there are more than two classes. For example, three classes are conceivable: a first class encompassing pairs in which the probability that they belong together is very high (e.g. greater than 90%), a second class encompassing pairs in which the probability that they belong together is very low (e.g. less than 10%), and a third class encompassing pairs which are not assignable to either the first or the second class. For the pairs of the third class, there is therefore a certain uncertainty as to whether $V_L$-$V_H$ pairs are concerned or not. The respective probabilities can be ascertained from the learning process with which the particular classification model has been created.

The model can, however, also be a regression model. The regression model can, for example, calculate for each pair of a $V_L$ gene and a $V_H$ gene on the basis of its feature vector the probability that the pair of the $V_L$ gene and the $V_H$ gene encode variable domains of light and heavy chains that belong to the same antibody and/or to the same antibody fragment. The result of the calculation of the regression model can, for example, be 0 when it is ruled out that the pair of the $V_L$ gene and the $V_H$ gene encode variable domains of light and heavy chains that belong to the same antibody and/or to the same antibody fragment; the result can, for example, be 1 or 100% when it is certain that the pair of the $V_L$ gene and the $V_H$ gene encode variable domains of light and heavy chains that belong to the same antibody and/or to the same antibody fragment. For the majority of pairs of a $V_L$ gene and a $V_H$ gene, the probability calculated will be between 0 and 1 or 0 and 100%.

The model (e.g. a classification model or a regression model) is preferably created on the basis of a self-learning algorithm. Particularly preferably, the model is created by means of supervised learning.

The model can, for example, be created using known antibodies and/or antibody fragments or using pairs of $V_L$ and the $V_H$ genes for which it is known whether they belong together or not. A model can be trained with these data (training data set).

For the creation of classification models, there is a multiplicity of methods, such as, for example, random forest or gradient boosting. For the creation of a regression model, there is likewise a multiplicity of methods, such as, for example, logistic regression. These and further methods for classification and regression are variously described in the prior art (see, for example, Norman Matloff: *Statistical Regression and Classification—From Linear Models to Machine Learning*, Texts in Statistical Science, CRC Press 2017, ISBN 978-1-4987-1091-6; Pratap Dangeti, *Statistics for Machine Learning*, Packt Publishing 2017, ISBN 978-1-78829-575-8).

The result of model creation is a model (e.g. a classification model or a regression model) which is also applicable to $V_L$ and the $V_H$ counts of unknown antibodies and/or antibody fragments. The higher the accuracy of the model, the more similar the training data set and the test data set. For example, the accuracy is higher when the same substrates (antigens) are used for training and the test and lower when different substrates are used.

Thus, for any pair of $V_L$ and $V_H$ genes, it can be stated, on the basis of the model, whether they belong together or not (with a defined probability). This information can be outputted in a next step. The output can, for example, be achieved on a screen of a computer. The information can also be printed out via a printer or stored in a data memory.

In a preferred embodiment, the selection method is a biopanning method and counts of the $V_L$ and $V_H$ genes in the pools from at least two selection cycles are used as features for the generation of feature vectors.

One starting point for a biopanning selection method is a first phage display library. The bacteriophages (phages for short) bear antibody fragments on their outer coats; at the same time, they bear in their interior the associated genes encoding the antibody fragments.

What must be identified and selected are those antibodies and/or antibody fragments which undergo an antigen-antibody reaction with one or more defined antigens. In particular, what must be identified and selected are those antibodies and/or antibody fragments which have a comparably high affinity for one epitope or for multiple epitopes of one or more antigens. Said high affinity becomes apparent in a particularly stable antigen-antibody complex having a high complexing constant.

It is also conceivable that antibodies and/or antibody fragments which bind selectively to various epitopes of one or more antigens must be identified and selected.

A biopanning method (biopanning for short) usually comprises multiple cycles (selection cycles).

One biopanning cycle comprises at least the following steps:
(1) providing a library of phages in which antibodies and/or antibody fragments are expressed as fusion polypeptides on phage coat proteins,
(2) incubating the phages with a substrate,
(3) separating the substrate-binding phages from the non-binding phages.

The binding phages are usually multiplied after step (3). The result is a new (second) phage display library which is, in turn, exposed to a substrate in order to separate the substrate-binding phages from the nonbinding phages, and so forth. However, it is also conceivable that the nonbinding phages are multiplied after step (3) and introduced to a further cycle.

It is conceivable that the selected phages differ with respect to their multiplication behavior. It is conceivable that differences in multiplication behavior lead to an enrichment effect with regard to phages which can be multiplied particularly well.

A substrate has antigens and/or antigen fragments which interact with the expressed antibody fragments of the phages, i.e. can form stable antigen-antibody complexes and hence bind the corresponding phages.

It is conceivable that the same substrate having the same antigens and/or antigen fragments is used in each cycle. In such a case, what occurs in the course of the cycles is an enrichment of antibodies and/or antibody fragments which interact strongly with the antigens and/or antigen fragments.

However, it is also conceivable that different substrates having different antigens and/or antigen fragments are used in individual cycles. One reason therefor can be that antibodies and/or antibody fragments having an affinity for multiple antigens and/or antigen fragments are to be selected.

Furthermore, it is conceivable that antibodies and/or antibody fragments which bind as little as possible to an antigen and/or antigen fragment are selected in a cycle.

At the end of a cycle, the genes of the antibodies and/or antibody fragments on the binding phages can be sequenced and the counts of the genes ascertained.

According to the invention, at least two selection cycles are passed through. If the selection cycles are arranged one above the other in the selection hierarchy, at least the following steps are passed through:
  (1) providing a library of phages in which antibodies and/or antibody fragments are expressed as fusion polypeptides on phage coat proteins,
  (2) incubating the phages with a substrate,
  (3) separating the substrate-binding phages from the nonbinding phages,
  (4) sequencing the genes of the antibodies and/or antibody fragments on the binding or nonbinding phages and ascertaining $V_L$ genes encoding the variable domains of light chains of the antibodies and/or antibody fragments and $V_H$ genes encoding the variable domains of the heavy chains of the antibodies and/or antibody fragments,
  (5) ascertaining the counts of the $V_L$ genes and the $V_H$ genes,
  (6) multiplying the binding or nonbinding phages and, in doing so, forming a new library of phages,
  (1') providing the new library of phages,
  (2') incubating the phages with a substrate,
  (3') separating the substrate-binding phages from the nonbinding phages,
  (4') sequencing the genes of the antibodies and/or antibody fragments on the binding or nonbinding phages and ascertaining $V_L$ genes encoding the variable domains of light chains of the antibodies and/or antibody fragments and $V_H$ genes encoding the variable domains of the heavy chains of the antibodies and/or antibody fragments,
  (5') ascertaining the counts of the $V_L$ genes and the $V_H$ genes.

The results present after passing through steps (1) to (5') are:
  selected antibodies and/or antibody fragments,
  sequences of the $V_L$ genes and the $V_H$ genes encoding the variable domains of light and heavy chains of the selected antibodies and/or antibody fragments,
  the count of the $V_L$ genes and the $V_H$ genes after passing through cycle (1')→(2')→(3') and also the counts of the $V_L$ genes and the $V_H$ genes after passing through the preceding cycle (1)→(2)→(3).

The counts (and optionally further features) ascertained in steps (5) and (5') can go into the formation of feature vectors. By means of a model (e.g. a classification model or a regression model), it is possible to ascertain for each pair of $V_L$ and $V_H$ genes whether they belong together or not.

A preferred embodiment of the method according to the invention therefore comprises the following steps:

(1) providing a library of phages in which antibodies and/or antibody fragments are expressed as fusion polypeptides on phage coat proteins,
  (2) incubating the phages with a substrate,
  (3) separating the substrate-binding phages from the nonbinding phages,
  (4) sequencing the genes of the antibodies and/or antibody fragments on the binding or nonbinding phages and ascertaining $V_L$ genes encoding the variable domains of light chains of the antibodies and/or antibody fragments and $V_H$ genes encoding the variable domains of the heavy chains of the antibodies and/or antibody fragments,
  (5) multiplying the binding or nonbinding phages and, in doing so, forming a new library of phages,
  (6) repeating steps (1) to (5) k times, step (4) being optional and each new library of phages from step (5) being used in step (1), k being an integer and greater than 0, and passage through steps (1) to (3) being one biopanning cycle,
  (7) forming feature vectors for pairs of $V_L$ genes and $V_H$ genes, the features used being at least the counts of the $V_L$ genes and the $V_H$ genes of the biopanning cycle last carried out and of a preceding biopanning cycle,
  (8) introducing the feature vectors to a model, the model calculating a result for each pair of a $V_L$ gene and a $V_H$ gene on the basis of its feature vector, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment,
  (9) outputting the result for each pair.

A preferred embodiment of the system according to the invention comprises:
  an input unit,
  a control unit,
  a feature vector generation unit,
  a calculation unit and
  an output unit,
  the control unit being configured to acquire, over at least two biopanning cycles in which antibodies and/or antibody fragments are selected, counts of $V_L$ genes encoding variable domains of light chains of the antibodies and/or antibody fragments and counts of $V_H$ genes encoding variable domains of heavy chains of the antibodies and/or antibody fragments via the input unit,
  the control unit being configured to prompt the feature vector generation unit to form feature vectors for pairs of the $V_L$ and $V_H$ genes, the features going into the formation of the feature vectors being at least the counts of the $V_L$ genes and the $V_H$ genes of a biopanning cycle and of a preceding biopanning cycle,
  the control unit being configured to prompt the calculation unit to calculate a result for each pair of a $V_L$ gene and a $V_H$ gene on the basis of its feature vector with the aid of a model, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment,
  the control unit being configured to prompt the output unit to output the result for each pair.

A preferred embodiment of the computer program product according to the invention comprises a data carrier, and program code which is stored on the data carrier and which prompts a computer, in the memory of which the program code is loaded, to execute the following steps:

acquiring counts of $V_L$ genes encoding variable domains of light chains of antibodies and/or antibody fragments and counts of $V_H$ genes encoding variable domains of heavy chains of the antibodies and/or antibody fragments over multiple cycles of a biopanning procedure in which the antibodies and/or antibody fragment are selected, forming feature vectors for pairs of the $V_L$ and $V_H$ genes, the features going into the formation of the feature vectors being at least the counts of the $V_L$ genes and the $V_H$ genes of a biopanning cycle and a preceding biopanning cycle, calculating a result for each pair of a $V_L$ gene and a $V_H$ gene on the basis of its feature vector with the aid of a model, the result specifying whether the $V_L$ gene and the $V_H$ gene encode variable domains which belong to the same antibody and/or to the same antibody fragment or whether the $V_L$ gene and the $V_H$ gene encode variable domains which do not belong to the same antibody and/or to the same antibody fragment, outputting the result for each pair.

Preferred embodiments of the present invention are:

1. A method comprising the steps of:
providing a library of antibodies and/or antibody fragments
introducing the antibodies and/or antibody fragments to a selection method, the selection method comprising at least two selection cycles, a first selection cycle and a second selection cycle
sequencing the genes of the antibodies and/or antibody fragments after the first selection cycle and after the second selection cycle and ascertaining $V_L$ genes encoding the variable domains of light chains of the antibodies and/or antibody fragments and $V_H$ genes encoding the variable domains of the heavy chains of the antibodies and/or antibody fragments
ascertaining features relating to the $V_L$ genes and $V_H$ genes from the first selection method and from the second selection method
forming feature vectors for pairs of $V_L$ genes and $V_H$ genes from the second selection cycle on the basis of the ascertained features from the first selection cycle and the second selection cycle
introducing the feature vectors to a classification model which performs for the respective pairs a classification into one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment
outputting information at least in relation to pairs in the first class.

2. The method according to embodiment 1, wherein antibodies and/or antibody fragments obtained from the first selection cycle are introduced to the second selection cycle optionally after passing through a multiplication step in which the obtained antibodies and/or antibody fragments are multiplied.

3. The method according to either of embodiments 1 and 2, wherein the selection method is a biopanning method.

4. The method according to any of embodiments 1 to 3, wherein the sequencing is carried out by means of a next-generation sequencing method.

5. The method according to any of embodiments 1 to 4, wherein the features relating to the $V_L$ genes and $V_H$ genes comprise the following features:
unambiguous identifiers of the ascertained $V_H$ genes,
unambiguous identifiers of the ascertained $V_L$ genes,
counts of the $V_H$ genes in the pool from the second selection cycle,
counts of the $V_L$ genes in the pool from the second selection cycle,
the counts of the $V_H$ genes in the pool from the first selection cycle, and
the counts of the $V_L$ genes in the pool from the first selection cycle.

6. The method according to any of embodiments 1 to 5, wherein one or more further features relating to the $V_L$ genes and $V_H$ genes are selected from the following list:
the absolute number of different $V_H$ genes in the pool from the second selection cycle
the absolute number of different $V_L$ genes in the pool from the second selection cycle
the absolute number of that $V_H$ gene which is present in the pool from the second selection cycle with the greatest count
the absolute number of that $V_L$ gene which is present in the pool from the second selection cycle with the greatest count
the relative count of the $V_H$ genes in the pool from the second selection cycle based on the number of the $V_H$ gene which occurs in the pool from the second selection cycle with the greatest count
the relative count of the $V_L$ genes in the pool from the second selection cycle based on the number of the $V_L$ gene which occurs in the pool from the second selection cycle with the greatest count
the differences between the counts of the $V_H$ genes in the pool from the second selection cycle and of the $V_L$ genes in the pool from the second selection cycle
the relative differences between the counts of the $V_H$ genes in the pool from the second selection cycle and the counts of the $V_L$ genes in the pool from the second selection cycle in relation to the count of the respective $V_H$ gene or $V_L$ gene in the pool from the second selection cycle that occurs with a greater count
the number of selection cycles which were passed through before the second selection cycle
the differences between the counts of the $V_H$ genes from the pool of the first selection cycle and the counts of the $V_L$ genes from the pool of the first selection cycle
the relative changes in the numbers of the $V_H$ genes from the first selection cycle to the second selection cycle
the relative changes in the numbers of the $V_L$ genes from the first selection cycle to the second selection cycle 7. The method according to any of embodiments 1 to 6, wherein the classification model has been created in a supervised learning method on the basis of known antibodies and/or antibody fragments.

8. The method according to any of embodiments 1 to 6, wherein the classification model is based on a random forest or gradient boosting method.

9. The method according to any of embodiments 1 to 8, comprising the following steps:
(1) providing a library of phages in which antibodies and/or antibody fragments are expressed as fusion polypeptides on phage coat proteins, (2) incubating the phages with a substrate,
(3) separating the substrate-binding phages from the non-binding phages,
(4) sequencing the genes of the antibodies and/or antibody fragments on the binding or nonbinding phages and ascertaining $V_L$ genes encoding the variable domains of light chains of the antibodies and/or antibody fragments and $V_H$ genes encoding the variable domains of the heavy chains of the antibodies and/or antibody fragments,
(5) ascertaining the counts of the $V_L$ genes and the $V_H$ genes,
(6) multiplying the binding or nonbinding phages and, in doing so, forming a new library of phages and repeating steps (1) to (5) n times, each new library of phages being used in step (1), n being an integer and greater than 0, and passage through steps (1) to (4) being one biopanning cycle,
(7) forming feature vectors for pairs of $V_L$ genes and $V_H$ genes, the features used being at least the counts of the $V_L$ genes and the $V_H$ genes of the current biopanning cycle and of a preceding biopanning cycle,
(8) introducing the feature vectors to a classification model which performs for the respective pairs a classification into one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment,
(9) outputting information at least in relation to pairs in the first class.

10. A system comprising:
an input unit,
a control and calculation unit,
a feature vector generation unit,
a classification unit, and
an output unit,
   the control and calculation unit being configured to acquire features relating to $V_L$ genes and $V_H$ genes encoding variable domains of light and heavy chains of antibodies and/or antibody fragments via the input unit,
   the antibodies and/or antibody fragments originating from a selection method comprising at least two selection cycles, a first selection cycle and a second selection cycle,
   the features comprising information relating to the $V_L$ genes and $V_H$ genes from the first selection cycle and from the second selection cycle,
the control and calculation unit being configured to prompt the feature vector generation unit to form feature vectors for pairs of $V_L$ and $V_H$ genes from the second selection cycle on the basis of the acquired features,
the control and calculation unit being configured to prompt the classification unit to assign the pairs of $V_L$ and $V_H$ genes on the basis of their feature vectors to one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment,
the control and calculation unit being configured to prompt the output unit to output at least information about pairs assigned to the first class.

11. The system according to embodiment 10, comprising comprising:
an input unit,
a control and calculation unit,
a feature vector generation unit,
a classification unit, and
an output unit,
   the control and calculation unit being configured to acquire, over multiple biopanning cycles in which antibodies and/or antibody fragments are selected, counts of $V_L$ genes encoding variable domains of light chains of the antibodies and/or antibody fragments and counts of $V_H$ genes encoding variable domains of heavy chains of the antibodies and/or antibody fragments via the input unit,
   the control and calculation unit being configured to prompt the feature vector generation unit to form feature vectors for pairs of the $V_L$ and $V_H$ genes, the features used being the counts of the $V_L$ genes and the $V_H$ genes of a biopanning cycle and of a preceding biopanning cycle,
   the control and calculation unit being configured to prompt the classification unit to assign the pairs of $V_L$ and $V_H$ genes on the basis of their feature vectors to one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment,
   the control and calculation unit being configured to prompt the output unit to output at least information about pairs assigned to the first class.

12. A computer program product comprising a data carrier, and program code which is stored on the data carrier and which prompts a computer, in the memory of which the program code is loaded, to execute the following steps:
   acquiring features relating to $V_L$ genes and $V_H$ genes encoding variable domains of light and heavy chains of antibodies and/or antibody fragments,
      the antibodies and/or antibody fragments originating from a selection method comprising at least two selection cycles, a first selection cycle and a second selection cycle,
      the features comprising information relating to the $V_L$ genes and $V_H$ genes from the first selection cycle and from the second selection cycle,
   forming feature vectors for pairs of $V_L$ and $V_H$ genes from the second selection cycle on the basis of the acquired features,
   assigning the pairs of $V_L$ and $V_H$ genes to one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment,
   outputting information at least about pairs assigned to the first class.

13. The computer program product according to embodiment 12, comprising a data carrier, and program code which is stored on the data carrier and which prompts a computer, in the memory of which the program code is loaded, to carry out one or more of the steps of a method according to any of embodiments 1 to 9.

14. The computer program product according to any of embodiments 12 to 13, comprising a data carrier, and program code which is stored on the data carrier and which prompts a computer, in the memory of which the program code is loaded, to execute the following steps:
  acquiring counts of $V_L$ genes encoding variable domains of light chains of antibodies and/or antibody fragments and counts of $V_H$ genes encoding variable domains of heavy chains of the antibodies and/or antibody fragments over multiple cycles of a biopanning procedure in which the antibodies and/or antibody fragment are selected,
  forming feature vectors for pairs of the $V_L$ and $V_H$ genes, the features used being at least the counts of the $V_L$ genes and the $V_H$ genes of a biopanning cycle and of a preceding biopanning cycle,
  introducing the feature vectors to a classification model which assigns pairs of the $V_L$ and $V_H$ genes on the basis of their feature vectors to one of at least two classes, a first class encompassing pairs in which the $V_L$ gene and the $V_H$ gene encode variable domains which belong to the same antibody and/or antibody fragment and a second class encompassing pairs in which the $V_L$ gene and the $V_H$ gene encode variable domains which do not belong to the same antibody and/or antibody fragment,
  outputting information at least about pairs assigned to the first class.

The invention is more particularly elucidated below with reference to examples and figures, without wishing to restrict the invention to the features and combinations of features that are mentioned in the examples or shown in the figures.

The following are shown:

FIG. 1 is described in detail further above.

Figure 1:
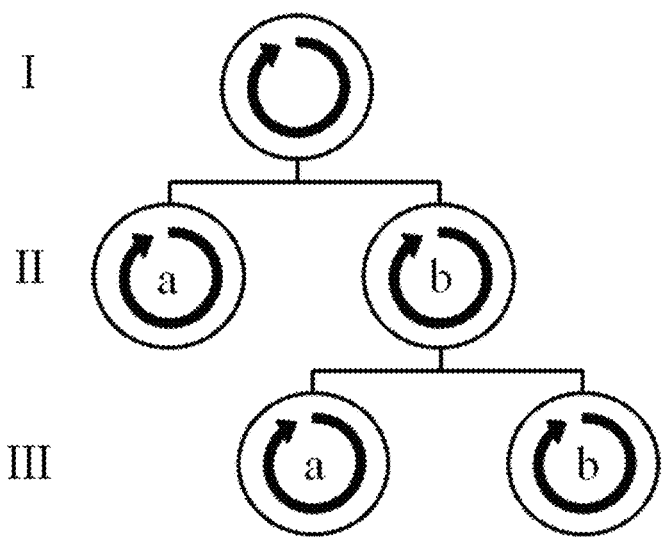
FIG. 1 shows an example of a selection hierarchy having three levels (I, II, III).

In a first step, a library (1) of phages (1a, 1b, 1c) in which antibodies and/or antibody fragments (10, 11, 12) are expressed as fusion polypeptides on phage coat proteins is provided.

In addition, a substrate (2) having immobilized antigens and/or antigen fragments is provided. The immobilized antigens and/or antigen fragments have binding sites (20) to which the antibodies and/or antibody fragments (10, 11, 12) of the phages (1a, 1b, 1c) can bind.

In step A of the biopanning cycle, the phages are incubated with the substrate.

In the course of this, interactions occur between the antibodies/antibody fragments and the antigens. In the present case, the antibody/antibody fragment (1c) exactly fits the binding site (20) of the immobilized antigen; the interaction and the resulting binding are comparatively strong (stronger than in the case of the other antibodies/antibody fragments).

In step B of the biopanning cycle, the phages which do not bind to the substrate or only bind weakly thereto are separated (washed off). What remain are the more strongly binding phages.

In step C of the biopanning cycle, the more strongly binding phages are detached from the substrate.

In step D of the biopanning cycle, the phages detached from the substrate are multiplied. The result is a new phage library which can be exposed again to a substrate.

From a portion of the phages detached from the substrate, the genes of the antibodies and/or antibody fragments can be sequenced (step E). This involves ascertaining the $V_L$ genes encoding the variable domains of light chains of the antibodies and/or antibody fragments and the $V_H$ genes encoding the variable domains of the heavy chains of the antibodies and/or antibody fragments and preferably also their counts.

Figure 2:
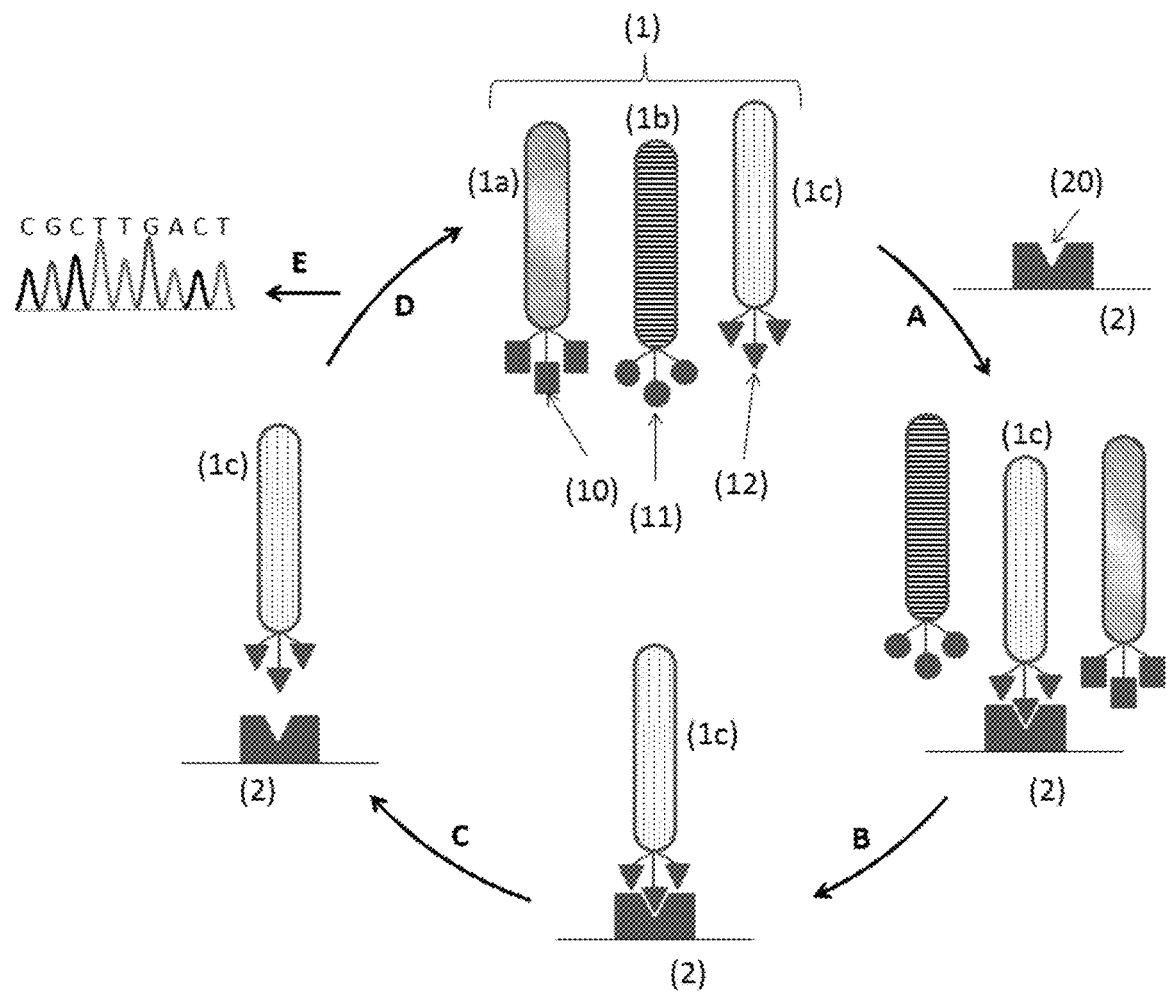
FIG. 2 shows schematically a biopanning cycle as an example of a selection cycle.
Figure 3:
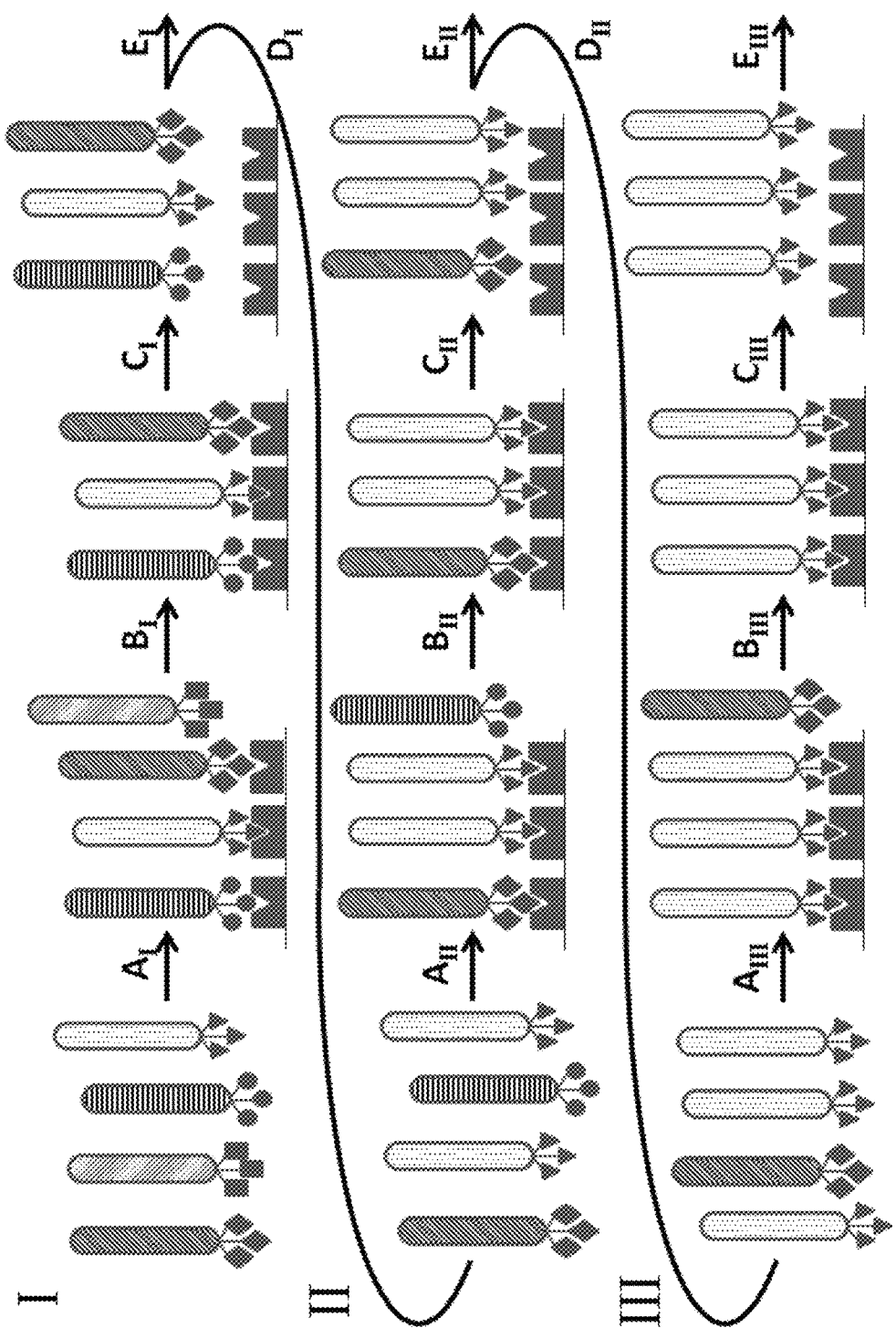

FIG. 3 shows schematically a biopanning procedure with three cycles (I, II, III). As in the present case, if the same substrate is used each time, the strongest binding antibodies/antibody fragments are further enriched with each cycle. Steps $A_I$, $B_I$, $C_I$, $D_I$, $E_I$ or $A_{II}$, $B_{II}$, $C_{II}$, $D_{II}$, $E_{II}$ or $A_{III}$, $B_{III}$, $C_{III}$, $D_{III}$, $E_{III}$ correspond to steps A, B, C, D, E in FIG. 2.

After each cycle (I, II, III), the $V_H$ and $V_L$ genes and their counts can be ascertained (steps $E_I$, $E_{II}$ and $E_{III}$).

Figure 4:
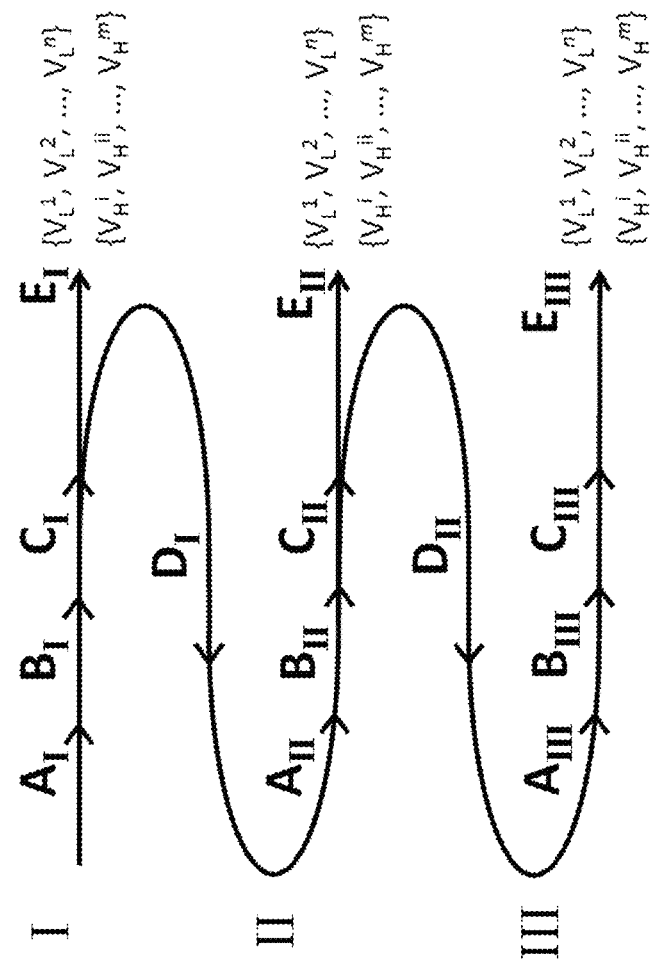

FIG. 4 shows schematically the same biopanning method as in FIG. 3 with cycles I, II and III and steps $A_I$, $A_{II}$, $A_{III}$, $B_I$, $B_{II}$, $B_{III}$, $C_I$, $C_{II}$, $C_{III}$, $D_I$, $D_{II}$, $D_{III}$, $E_I$, $E_{II}$ and $E_{III}$. The result of steps $E_I$, $E_{II}$ and $E_{III}$ is a quantity of $V_L$ genes $\{V_L^1, V_L^2, \ldots, V_L^n\}$ and a quantity of $V_H$ genes $\{V_H^i, V_H^{ii}, \ldots, V_H^m\}$; each gene is identifiable on the basis of an unambiguous identifier (1, 2, ... to n or i, ii, ... to m).

Figure 5:
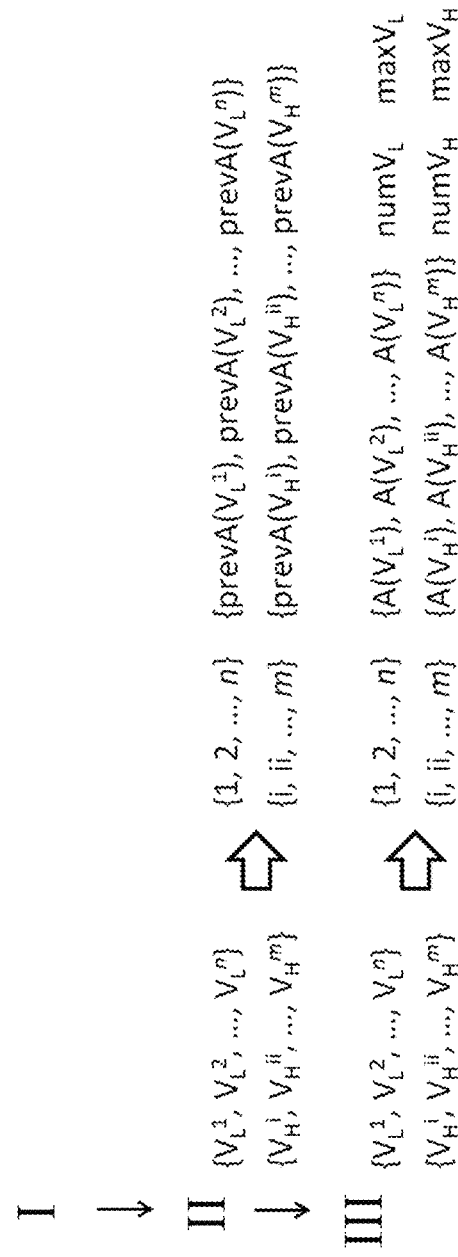

FIG. 5 shows by way of example the generation/acquisition of features relating to $V_L$ genes and $V_H$ genes. Three sequencing cycles (I, II, III) were passed through. Following selection cycles II and III, the $V_L$ genes and the $V_H$ genes were sequenced.

In the present example, selection cycle II is the "first selection cycle" and selection cycle III is the "second selection cycle" in the context of the present invention.

Features relating to the $V_L$ genes and $V_H$ genes are, for example, the unambiguous identifiers ($\{1, 2, \ldots, n\}$ and $\{i, ii, \ldots, m\}$).

Further features relating to the $V_L$ genes and $V_H$ genes are, for example, the counts of the $V_L$ genes in the pool from the second selection cycle $\{A(V_L^1), A(V_L^2), \ldots, A(V_L^n)\}$ and of the $V_H$ genes in the pool from the second selection cycle $\{A(V_H^i), A(V_H^{ii}), \ldots, A(V_H^m)\}$.

Further features relating to the $V_L$ genes and $V_H$ genes are, for example, the counts of the $V_L$ genes in the pool from the first selection cycle $\{\text{prev}A(V_L^1), \text{prev}A(V_L^2), \ldots, \text{prev}A(V_L^n)\}$ and of the $V_H$ genes in the pool from the first selection cycle $\{\text{prev}A(V_H^i), \text{prev}A(V_H^{ii}), \ldots, \text{prev}A(V_H^m)\}$.

Further features relating to the $V_L$ genes and $V_H$ genes are, for example, the absolute numbers of different $V_L$ genes (num$V_L$) and different $V_H$ genes (num$V_H$) in the pool from the second selection cycle.

Further features relating to the $V_L$ genes and $V_H$ genes are, for example, the absolute number (count) of that $V_H$ gene which is present in the pool from the second selection cycle with the greatest count (max$V_H$) and the absolute number (count) of that $V_L$ gene which is present in the pool from the second selection cycle with the greatest count (max$V_L$).

Further features can be calculated from the described features, such as, for example:

$$\text{rel}V_H = A(V_H)/\text{max}V_H$$

$$\text{rel}V_L = A(V_L)/\text{max}V_L$$

$$\text{diff} = |A(V_H) - A(V_L)|$$

$$\text{reldiff} = |A(V_H) - A(V_L)|/\text{Max}(A(V_H), A(V_L))$$

$$\text{prevdiff} = |\text{prev}A(V_H) - \text{prev}A(V_L)|$$

$$\text{prevRelDiff}V_H = (|A(V_H) - \text{prev}A(V_H)|)/\text{Max}((A(V_H), \text{prev}A(V_H)))$$

$$\text{prevRelDiff}V_L = (|A(V_L) - \text{prev}A(V_L)|)/\text{Max}((A(V_L), \text{prev}A(V_L)))$$

The stated features and/or further/other features are used for generating feature vectors. This is depicted schematically in FIG. 6.

Figure 6:
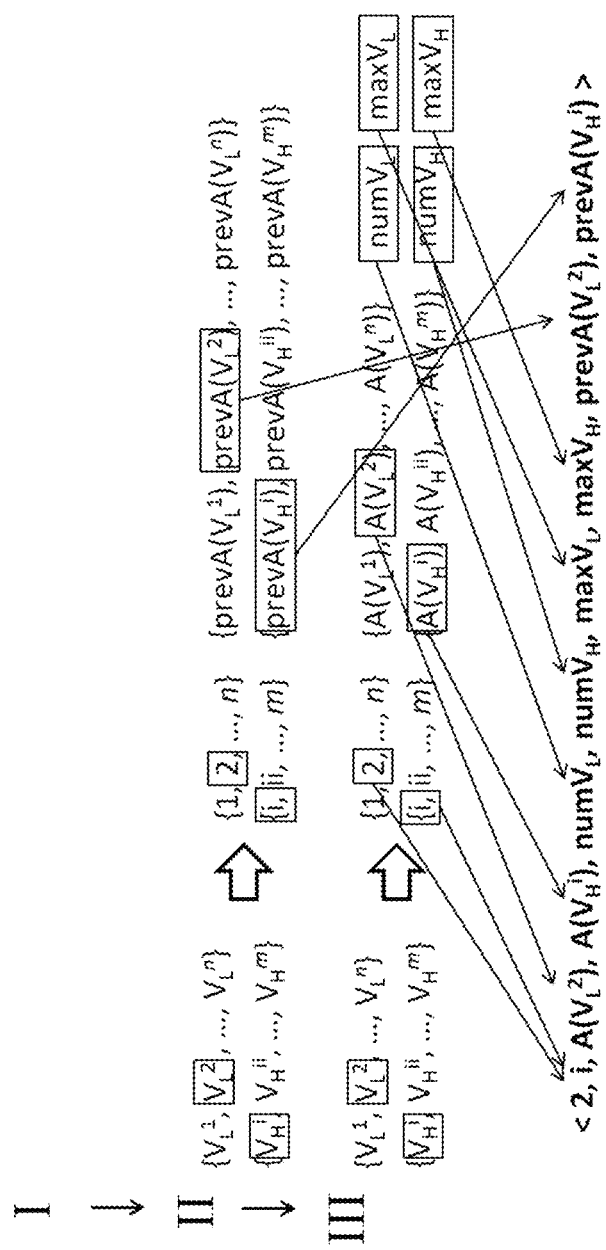

FIG. 6 shows by way of example the generation of a feature vector for a pair $(V_L^x, V_H^y)$ of a $V_L$ gene and a $V_H$ gene.

The feature vector is generated for the pair $V_L^2$ and $V_H^i$.
Features which have gone into the feature vector:
the identifier of the $V_L^2$ gene: 2
the identifier of the $V_H^i$ gene: i
the count of the $V_L^2$ gene in the pool from the second selection cycle: $A(V_L^2)$
the count of the $V_H^i$ gene in the pool from the second selection cycle: $A(V_H^i)$
the count of the $V_L^2$ gene in the pool from the first selection cycle: $\text{prev}A(V_L^2)$
the count of the $V_H^i$ gene in the pool from the first selection cycle: $\text{prev}A(V_H^i)$
the absolute number of different $V_L$ genes in the pool from the second selection cycle: $\text{num}V_L$
the absolute number of different $V_H$ genes in the pool from the second selection cycle: $\text{num}V_H$
the count of that $V_H$ gene which is present in the pool from the second selection cycle with the greatest count: $\text{max}V_H$
the count of that $V_L$ gene which is present in the pool from the second selection cycle with the greatest count: $\text{max}V_L$.

A preferred feature vector for an arbitrary pair of a $V_L^x$ gene and a $V_H^y$ gene having the respective identifiers x and y is:

$<x, y, A(V_L^x), A(V_H^y), \text{diff}^{(x,y)}, \text{reldiff}^{(x,y)}, \text{rel}V_L^x, \text{rel}V_H^y, \text{num}V_H, \text{num}V_L, \text{max}V_H, \text{max}V_L, \text{prevnum}, \text{prev}A(V_L^x), \text{prev}A(V_H^y), \text{prevdiff}^{(x,y)}, \text{prevRelDiff}V_L^x, \text{prevRelDiff}V_H^y>$ A particularly preferred feature vector for an arbitrary pair of a $V_L^x$ gene and a $V_H^y$ gene having the respective identifiers x and y is:

$<x, y, A(V_L^x), A(V_H^y), \text{diff}^{(x,y)}, \text{reldiff}^{(x,y)}, \text{rel}V_L^x, \text{rel}V_H^y, \text{prevdiff}^{(x,y)}, \text{prevRelDiff}V_L^x, \text{prevRelDiff}V_H^y>$ The orders in which the features occur in the feature vectors described here can of course also be different to the orders presented here.

FIG. 7 shows by way of example a rule-based classifier which can be a result of the generation of a classification model.

For a pair $(V_L^x, V_H^y)$ of a $V_L$ gene and a $V_H$ gene, conditions (1) to (14) are checked one after another. If condition (1) applies, the pair is not a $V_L$-$V_H$ pair (CLASS=neg). The classification is completed. If condition (1) does not apply, condition (2) is checked. If condition (2) applies, the pair is not a $V_L$-$V_H$ pair (CLASS=neg). The classification is completed. If condition (2) does not apply, condition (3) is checked, and so forth.

If conditions (1) to (14) do not apply, the pair is a $V_L$-$V_H$ pair (CLASS=pos).

Figure 8:
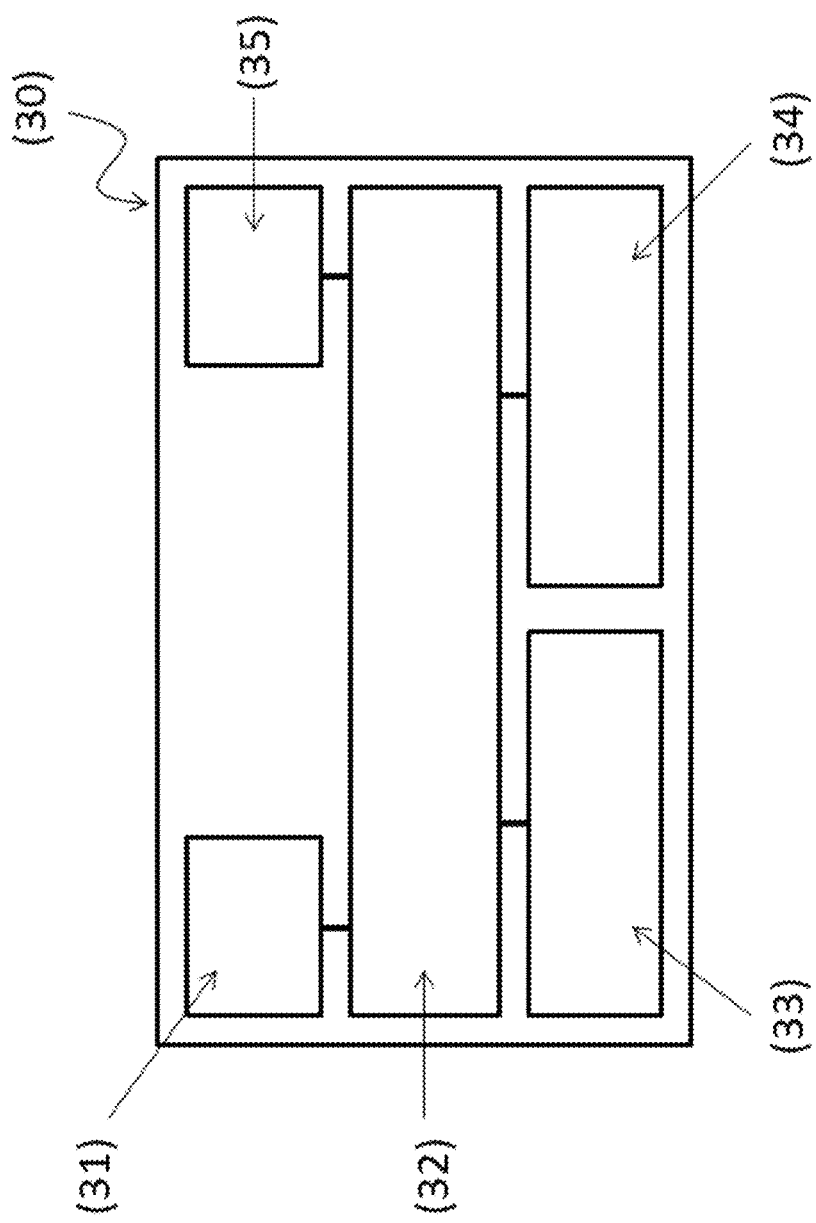

FIG. 8 shows schematically one embodiment of the system according to the invention.

The system (30) comprises an input unit (31), a control unit (32), a feature vector generation unit (33), a calculation unit (34), and an output unit (35).

Information is introduced into the system (30) via the input unit (31). Usually, the input unit (31) also serves as a communication interface with a user of the system (30). The input unit (31) can comprise a keyboard, a mouse, a touchscreen, a microphone, a network connection, a connection to a data memory, a connection to a device and/or the like. In particular, it is via the input unit (31) that features relating to $V_L$ genes and $V_H$ genes encoding variable domains of light and heavy chains of antibodies and/or antibody fragments are introduced into the system in order to be further processed there. In this connection, this information can be input manually by a user via a user interface and/or read automatically via an interface from a data memory and/or a connected device and/or device connected to the system (30) via a network (e.g. a sequencing device). It is conceivable that only some of the features relating to $V_L$ genes and $V_H$ genes are introduced via the input unit (31), whereas other features relating to $V_L$ genes and $V_H$ genes are calculated from the introduced features by the control unit (32) and/or the feature vector generation unit (33).

The control unit (32) serves to control the components of the system (30) and to coordinate the data and signal flows between the components and between the system (30) and external devices. The control unit (32) usually comprises a memory in which the computer program according to the invention can be loaded in order to execute one or more steps of the method according to the invention.

From the features relating to the $V_L$ genes and $V_H$ genes, the feature vector generation unit (33) generates feature vectors for individual pairs of $V_L$ genes and $V_H$ genes. The feature vector generation unit (33) can be part of the control unit (32) or a unit independent thereof. It is also conceivable that feature vectors are introduced into the system (30) via the input unit (31).

The calculation unit (34) carries out a calculation of a result. The result specifies whether a pair of a $V_L$ gene and a $V_H$ gene encode variable domains which belong to the same antibody and/or to the same antibody fragment or do not belong to the same antibody and/or to the same antibody fragment. The calculation is done on the basis of the feature vector of the pair. The calculation is done with the aid of a model. For example, if the model is a classification model, the calculation is a classification and the result is an assignment of the pair to a class. If the calculation model is a regression model, the calculation is a regression and the result is a probability that the $V_L$ gene and the $V_H$ gene of the pair encode variable domains which belong to the same antibody and/or to the same antibody fragment.

A classification model assigns the respective pair on the basis of the respective feature vector to one of at least two classes, a first class encompassing pairs in which the $V_L$ gene and the $V_H$ gene encode variable domains which belong to the same antibody and/or antibody fragment (CLASS=pos) and a second class encompassing pairs in which the $V_L$ gene and the $V_H$ gene encode variable domains which do not belong to the same antibody and/or antibody fragment (CLASS=neg).

A regression model calculates for the respective pair on the basis of the respective feature vector a number specifying the probability that the $V_L$ gene and a $V_H$ gene of the pair encode variable domains which belong to the same antibody and/or antibody fragment.

The calculation unit (34) can be part of the control unit (32) and/or part of the feature vector generation unit (33) and/or an independent unit.

The result of the calculation of the calculation unit (34) is output via the output unit (35). The output is preferably made to the user of the system (30). The output unit can comprise a screen, a printer, a loudspeaker, a data memory, a connection to a network, a connection to a device and/or the like.

The system according to the invention can, for example, be configured as a computer (e.g. desktop computer, tablet computer, smartphone, server) or a combination of computers.

What is claimed is:

1. A method of identifying pairs of genes which encode $V_L$-$V_H$ pairs of antibodies and/or antibody fragments, the method comprising the steps of:
   selecting the antibodies and/or antibody fragments from a library by a selection method comprising at least two selection cycles including a first selection cycle and a second selection cycle, each of the first selection cycle and the second selection cycle including at least one of a biopanning procedure or an immunization procedure;
   sequencing the genes encoding the antibodies and/or antibody fragments after the first selection cycle and after the second selection cycle and ascertaining $V_L$ genes encoding variable domains of light chains of the antibodies and/or antibody fragments and $V_H$ genes encoding variable domains of heavy chains of the antibodies and/or antibody fragments, wherein sequencing the genes includes sequence determination according to at least one of a Sanger dideoxy method and a next-generation sequencing (NGS) method;
   ascertaining features relating to the $V_L$ genes and $V_H$ genes from the first selection cycle and from the second selection cycle, the features relating to the $V_L$ genes and $V_H$ genes comprising the following features:
     counts of the $V_H$ genes in a pool from the second selection cycle;
     counts of the $V_L$ genes in the pool from the second selection cycle;
     counts of the $V_H$ genes in a pool from the first selection cycle; and
     counts of the $V_L$ genes in the pool from the first selection cycle;
   forming feature vectors for pairs of $V_L$ genes and $V_H$ genes from the second selection cycle on the basis of the ascertained features from the first selection cycle and the second selection cycle;
   introducing the feature vectors to a model, the model calculating a result for each pair of a $V_L$ gene and a $V_H$ gene on the basis of its feature vector, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and
   outputting the result in a report.

2. The method of claim 1, wherein antibodies and/or antibody fragments obtained from the first selection cycle are introduced to the second selection cycle after passing through a multiplication step in which the obtained antibodies and/or antibody fragments are multiplied.

3. The method of claim 1, wherein the selection method is a biopanning method.

4. The method of claim 1, wherein the sequencing is carried out by means of a next-generation sequencing method.

5. The method of claim 1, wherein one or more further features relating to the $V_L$ genes and $V_H$ genes go into the formation of the feature vectors, the one or more further features being selected from the following list:

the absolute number of different $V_H$ genes in the pool from the second selection cycle;
the absolute number of different $V_L$ genes in the pool from the second selection cycle;
the absolute number of the $V_H$ gene which is present in the pool from the second selection cycle with the greatest count;
the absolute number of the $V_L$ gene which is present in the pool from the second selection cycle with the greatest count;
the relative count of the $V_H$ genes in the pool from the second selection cycle based on the number of the $V_H$ gene which occurs in the pool from the second selection cycle with the greatest count;
the relative count of the $V_L$ genes in the pool from the second selection cycle based on the number of the $V_L$ gene which occurs in the pool from the second selection cycle with the greatest count;
the differences between the counts of the $V_H$ genes in the pool from the second selection cycle and the $V_L$ genes in the pool from the second selection cycle;
the relative differences between the counts of the $V_H$ genes in the pool from the second selection cycle and the $V_L$ genes in the pool from the second selection cycle in relation to the count of the respective $V_H$ gene or $V_L$ gene in the pool from the second selection cycle that occurs with a greater count;
the number of selection cycles which were passed through before the second selection cycle;
the differences between the counts of the $V_H$ genes from the pool of the first selection cycle and the $V_L$ genes from the pool of the first selection cycle;
the relative changes in the numbers of the $V_H$ genes from the first selection cycle to the second selection cycle; and
the relative changes in the numbers of the $V_L$ genes from the first selection cycle to the second selection cycle.

6. The method of claim 1, wherein the model has been created in a supervised learning method on the basis of features of $V_H$ genes and $V_L$ genes of which it is known which belong together and which do not belong together.

7. The method of claim 1, wherein the model is a classification model or a regression model.

8. The method of claim 1, further comprising the following steps:
   (1) providing a library of phages in which antibodies and/or antibody fragments are expressed as fusion polypeptides on phage coat proteins;
   (2) incubating the phages with a substrate;
   (3) separating the substrate-binding phages from the non-binding phages;
   (4) sequencing the genes of the antibodies and/or antibody fragments on the binding or nonbinding phages and ascertaining $V_L$ genes encoding the variable domains of light chains of the antibodies and/or antibody fragments and $V_H$ genes encoding the variable domains of the heavy chains of the antibodies and/or antibody fragments;
   (5) multiplying the binding or nonbinding phages and, in doing so, forming a new library of phages and repeating steps (1) to (5) k times, each new library of phages being used in step (1), k being an integer and greater than 0, and passage through steps (1) to (4) being one biopanning cycle;
   (6) forming feature vectors for pairs of $V_L$ genes and $V_H$ genes, the features used being at least the counts of the $V_L$ genes and the $V_H$ genes of the biopanning cycle last carried out and of a preceding biopanning cycle;

(7) introducing the feature vectors to a model, said model calculating a result for each pair of a $V_L$ gene and a $V_H$ gene on the basis of its feature vector, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and (8) outputting the result for each pair.

9. A system for identifying pairs of genes which encode $V_L$-$V_H$ pairs of antibodies and/or antibody fragments, the system comprising:

memory storing computer-executable instructions; and a computer which executes the computer-executable instructions stored in memory to:

acquire features relating to $V_L$ genes and $V_H$ genes encoding variable domains of light and heavy chains of antibodies and/or antibody fragments, wherein genes of the antibodies and/or antibody fragments are sequenced according to at least one of a Sanger dideoxy method and a next-generation sequencing (NGS) method;

wherein the antibodies and/or antibody fragments originate from a selection method comprising at least two selection cycles, the at least two selection cycles including a first selection cycle and a second selection cycle, each of the first selection cycle and the second selection cycle including at least one of a biopanning procedure or an immunization procedure; and wherein the features relating to the $V_L$ genes and $V_H$ genes comprise the following features:

counts of the $V_H$ genes in a pool from the second selection cycle;

counts of the $V_L$ genes in the pool from the second selection cycle;

counts of the $V_H$ genes in a pool from the first selection cycle; and counts of the $V_L$ genes in the pool from the first selection cycle;

form feature vectors for pairs of $V_L$ and $V_H$ genes from the second selection cycle on the basis of the acquired features;

calculate a result for each pair of a $V_L$ gene and a $V_H$ gene on the basis of its feature vector with the aid of a model, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and output the result in a report.

10. The system of claim 9, wherein the computer executes the computer-executable instructions stored in memory to:

acquire, over at least two biopanning cycles in which antibodies and/or antibody fragments are selected, counts of $V_L$ genes encoding variable domains of light chains of the antibodies and/or antibody fragments and counts of $V_H$ genes encoding variable domains of heavy chains of the antibodies and/or antibody fragments;

form feature vectors for pairs of the $V_L$ and $V_H$ genes, the features used being the counts of the $V_L$ genes and the $V_H$ genes of a biopanning cycle and of a preceding biopanning cycle;

calculate a result for each pair of a $V_L$ gene and a $V_H$ gene on the basis of its feature vector with the aid of a model, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and output the result for each pair.

11. A non-transitory computer-readable storage medium comprising program code, which when executed by at least one processor, causes the at least one processor to perform the following steps:

acquiring features relating to $V_L$ genes and $V_H$ genes encoding variable domains of light and heavy chains of antibodies and/or antibody fragments, wherein genes of the antibodies and/or antibody fragments are sequenced according to at least one of a Sanger dideoxy method and a next-generation sequencing (NGS) method;

wherein the antibodies and/or antibody fragments originate from a selection method comprising at least two selection cycles including a first selection cycle and a second selection cycle, each of the first selection cycle and the second selection cycle including at least one of a biopanning procedure or an immunization procedure; and wherein the features relating to the $V_L$ genes and $V_H$ genes comprise the following features:

counts of the $V_H$ genes in a pool from the second selection cycle;

counts of the $V_L$ genes in the pool from the second selection cycle;

counts of the $V_H$ genes in a pool from the first selection cycle; and counts of the $V_L$ genes in the pool from the first selection cycle;

forming feature vectors for pairs of $V_L$ and $V_H$ genes from the second selection cycle on the basis of the acquired features;

calculating a result for each pair of a $V_L$ gene and a $V_H$ gene on the basis of its feature vector with the aid of a model, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and outputting the result in a report.

12. The non-transitory computer-readable storage medium of claim 11, wherein the program code, when executed by the at least one processor, further causes the at least one processor to perform the following steps:

acquiring counts of $V_L$ genes encoding variable domains of light chains of antibodies and/or antibody fragments and counts of $V_H$ genes encoding variable domains of heavy chains of the antibodies and/or antibody fragments over multiple cycles of a biopanning procedure in which the antibodies and/or antibody fragment are selected;

forming feature vectors for pairs of the $V_L$ and $V_H$ genes, the features used being at least the counts of the $V_L$ genes and the $V_H$ genes of a biopanning cycle and of a preceding biopanning cycle;

calculating a result for each pair of a $V_L$ gene and a $V_H$ gene on the basis of its feature vector with the aid of a model, the result specifying whether the $V_L$ gene and the $V_H$ gene encode variable domains which belong to the same antibody and/or antibody fragment or whether the $V_L$ gene and the $V_H$ gene encode variable domains which do not belong to the same antibody and/or antibody fragment; and outputting the result for each pair.

13. The non-transitory computer-readable storage medium of claim 11, wherein the antibodies and/or antibody fragments are obtained from the first selection cycle and then introduced to the second selection cycle after passing through a multiplication step in which the obtained antibodies and/or antibody fragments are multiplied.

14. The non-transitory computer-readable storage medium of claim 11, wherein the selection method is a biopanning method.

15. The non-transitory computer-readable storage medium of claim 11, wherein the sequencing is carried out by means of a next-generation sequencing method.

16. The non-transitory computer-readable storage medium of claim 11, wherein the features relating to the $V_L$ genes and $V_H$ genes further include one or more of the following:

the absolute number of different $V_H$ genes in the pool from the second selection cycle;

the absolute number of different $V_L$ genes in the pool from the second selection cycle;

the absolute number of the $V_H$ gene which is present in the pool from the second selection cycle with the greatest count;

the absolute number of the $V_L$ gene which is present in the pool from the second selection cycle with the greatest count;

the relative count of the $V_H$ genes in the pool from the second selection cycle based on the number of the $V_H$ gene which occurs in the pool from the second selection cycle with the greatest count;

the relative count of the $V_L$ genes in the pool from the second selection cycle based on the number of the $V_L$ gene which occurs in the pool from the second selection cycle with the greatest count;

the differences between the counts of the $V_H$ genes in the pool from the second selection cycle and the $V_L$ genes in the pool from the second selection cycle;

the relative differences between the counts of the $V_H$ genes in the pool from the second selection cycle and the $V_L$ genes in the pool from the second selection cycle in relation to the count of the respective $V_H$ gene or $V_L$ gene in the pool from the second selection cycle that occurs with a greater count;

the number of selection cycles which were passed through before the second selection cycle;

the differences between the counts of the $V_H$ genes from the pool of the first selection cycle and the $V_L$ genes from the pool of the first selection cycle;

the relative changes in the numbers of the $V_H$ genes from the first selection cycle to the second selection cycle; and the relative changes in the numbers of the $V_L$ genes from the first selection cycle to the second selection cycle.

17. The non-transitory computer-readable storage medium of claim 11, wherein the model has been created in a supervised learning method on the basis of features of $V_H$ genes and $V_L$ genes of which it is known which belong together and which do not belong together.

18. The non-transitory computer-readable storage medium of claim 11, wherein the model is a classification model or a regression model.

* * * * *